(12) United States Patent
Chen et al.

(10) Patent No.: US 9,943,227 B2
(45) Date of Patent: Apr. 17, 2018

(54) SELECTIVE DATA TRANSMISSION METHOD AND SYSTEM BASED ON CENTRAL MONITORING SYSTEM

(71) Applicant: EDAN INSTRUMENTS, INC, Shenzhen, Guangdong Province (CN)

(72) Inventors: Wusun Chen, Shenzhen (CN); Lin Tang, Shenzhen (CN); Xin Yin, Shenzhen (CN)

(73) Assignee: EDAN INSTRUMENTS, INC, Shenzhen, Guangdong (CN)

( * ) Notice: Subject to any disclaimer, the term of this patent is extended or adjusted under 35 U.S.C. 154(b) by 0 days.

(21) Appl. No.: 14/903,063

(22) PCT Filed: Dec. 10, 2013

(86) PCT No.: PCT/CN2013/088930
§ 371 (c)(1),
(2) Date: Jan. 6, 2016

(87) PCT Pub. No.: WO2015/058442
PCT Pub. Date: Apr. 30, 2015

(65) Prior Publication Data
US 2016/0183791 A1    Jun. 30, 2016

(30) Foreign Application Priority Data

Oct. 21, 2013 (CN) .......................... 2013 1 0496654

(51) Int. Cl.
*G08C 19/22* (2006.01)
*H04Q 9/00* (2006.01)
(Continued)

(52) U.S. Cl.
CPC .......... *A61B 5/0002* (2013.01); *A61B 5/0022* (2013.01); *G06F 19/3418* (2013.01);
(Continued)

(58) Field of Classification Search
CPC ...................... G06F 19/322; A61B 2560/0475
(Continued)

(56) References Cited

U.S. PATENT DOCUMENTS

2011/0178462 A1* 7/2011 Moberg ............... A61B 5/0002
604/151
2012/0016305 A1* 1/2012 Jollota ............... A61B 5/14532
604/151
(Continued)

*Primary Examiner* — Fabricio R Murillo Garcia
(74) *Attorney, Agent, or Firm* — JCIPRNET

(57) ABSTRACT

The present invention provides a selective data transmission method and a system based on a central monitoring system. The selective data transmission method includes a wireless sensor, wherein the wireless sensor executes the following steps of: A. collecting data; B. sending the data to a designated receiving end; C. selecting a receiving end according to an instruction, and taking the receiving end as the designated receiving end; and D. establishing a wireless connection with the designated receiving end. The present invention has the advantageous effects that the method and the system realize selective data transmission through transmitting the data to a selected receiving end, which not only can be applied to the field of medical monitoring, but also can be applied to such fields as security prevention, data backup and the like; working nodes can be switched.

16 Claims, 4 Drawing Sheets

(51) Int. Cl.
  *A61B 5/00* (2006.01)
  *G06F 19/00* (2018.01)
(52) U.S. Cl.
  CPC ........... *H04Q 9/00* (2013.01); *H04Q 2209/10* (2013.01); *H04Q 2209/40* (2013.01); *H04Q 2209/823* (2013.01)
(58) Field of Classification Search
  USPC .................................................. 340/870.07
  See application file for complete search history.

(56) References Cited

U.S. PATENT DOCUMENTS

2012/0198341 A1* 8/2012 Pekarske ............... G06F 3/0481
  715/733
2015/0359429 A1* 12/2015 Al-Ali .................... A61B 5/002
  600/476

* cited by examiner

SELECTIVE DATA TRANSMISSION METHOD AND SYSTEM BASED ON CENTRAL MONITORING SYSTEM

CROSS REFERENCE TO RELATED APPLICATIONS

The present application is the US national stage of International Patent Application PCT/CN2013/088930 filed on Dec. 10, 2013, which, in turn, claims priority to Chinese Patent Application CN 201310496654.3 filed on Oct. 21, 2013.

FIELD OF THE INVENTION

The present invention relates to a data transmission processing method and a system, and more particularly, to a selective data transmission method and a system based on a central monitoring system.

BACKGROUND OF THE INVENTION

A traditional pregnant woman central monitoring system consists of a central station and a monitor in a networking manner. The monitor is responsible for collecting such parameters as fetal heart rate, uterine pressure, fetal movement, maternal eletrocardiogram, blood oxygen, non-invasive blood pressure, pulse, respiration, body temperature and the like. The monitor transmits data to the central station via a wired or wireless network. The central station displays the number and waveforms of multiple monitors on the same screen. The central station supports such functions as alarm, storage, review, printing, marking, sufferer information management, archive management and the like. The central station can be equipped with multiple observation stations, and supports distributed application.

After the appearance of a wireless transducer technology, application modes of a wireless sensor+a central station (the wireless sensor directly transmits data to the central station, hereinafter referred to as a central monitoring mode), a wireless sensor+a monitor+a central station (the wireless sensor firstly transmits data to the monitor, and then the monitor transmits the data to the central station, hereinafter referred to as a bedside monitoring mode) are generated. The mode of wireless sensor+central station is applied to a pregnant woman in good health conditions. After the sensor is bound to the pregnant woman, the pregnant woman can walk freely, and medical care personnel does not need to conduct bedside monitoring on the pregnant woman in an intensive care unit, and only needs to directly monitor at the central station. The mode of wireless sensor+monitor+central station is applied to a pregnant woman in poor health conditions. The medical care personnel needs to conduct bedside monitoring on the pregnant woman in the intensive care unit, and meanwhile needs to monitor at the central station. However, the health condition of the pregnant woman during the monitoring process is changed dynamically. An abnormality situation may possibly occur to a pregnant woman in a well health condition originally, and a pregnant woman originally in an abnormal condition may recover well. The present monitoring mode cannot change conveniently and intelligently according to the health conditions of the pregnant woman, and thus has defects.

Since the present monitoring mode cannot be changed, i.e., the wireless sensor can only work in two modes (i.e., wireless sensor+central station, and wireless sensor+monitor+central station, wherein the two modes cannot be switched), the wireless sensor can only work in a single mode, and the data transmitted out by the wireless sensor cannot select a receiver, the working manner is single, and mode switching cannot be conducted; therefore, it is inconvenient for users to use.

SUMMARY OF THE INVENTION

In order to solve the problems in the prior art that the wireless sensor has single working manner, and cannot switch modes, the present invention provides a selective data transmission method based on a central monitoring system.

The present invention provides a selective data transmission method based on a selective data transmission method, wherein the selective data transmission method includes a wireless sensor, and the wireless sensor executes the following steps of:

A. collecting data;
B. sending the data to a designated receiving end, the designated receiving end being a central station or a monitor;
C. selecting a receiving end according to an instruction of the central station, and taking the receiving end as the designated receiving end; and
D. establishing a wireless connection with the designated receiving end; and
E. returning to execute step A;

judging whether a bedside monitoring instruction of the central station is received in step C; if yes, then executing a bedside monitoring mode step; otherwise, executing a central monitoring mode step;

the bedside monitoring mode step including the following steps of:

C1. establishing a wireless connection with the monitor, and taking the monitor as the designated receiving end; and
C2. returning to execute step A;

the central monitoring mode step including the following steps of:

judging whether a central monitoring instruction of the central station is received; if yes, then executing CC1 step; otherwise, returning to execute step A;

CC1. establishing a wireless connection with the central station, and taking the central station as the designated receiving end; and
CC2. returning to execute step A;

in the step B, if the designated receiving end is the monitor, then after the wireless sensor sends the data to the monitor, the monitor transmits the received data to the central station.

As a further improvement of the present invention, the bedside monitoring mode step further includes generating a warning signal to make the wireless sensor alarm.

As a further improvement of the present invention, before the step A, the method further includes the following two steps of:

a wireless sensor configuration step: the following configuration information is saved in the wireless sensor: a wireless sensor device number, an IP address and a port number of the central station, as well an IP address and a port number of the monitor; wherein the wireless sensor device number is configured to control data parameters of the wireless sensor to be displayed in a sub-window corresponding to the device number on the central station; the IP address and the port number of the central station are configured to establish a TCP connection between the wireless sensor and the central station; the IP address and the port number of the monitor are configured to establish a TCP connection between the wireless sensor and the monitor; and the configuration information is read after the wireless sensor is electrified and enabled; and a step of establishing a TCP connection between the wireless sensor and the central station: the wireless sensor sends a connection request to the IP address and the port number of the central station, and establishes a TCP connection, wherein the wireless sensor communicates with the central station using a client/server mode, the wireless sensor being a client, and the central station being a server.

As a further improvement of the present invention, the selective data transmission method further includes a central station, wherein the central station includes all wireless sensor device number and monitor device number, the central station intercepts a TCP port number, receives a connection request from the wireless sensor and the monitor, and establishes a TCP connection; and the central station establishes an independent TCP communication channel for each new connection request, so that the central station is capable of receiving the network data of multiple sets of wireless sensors and multiple sets of monitors simultaneously; and the wireless sensor and the monitor communicate with the central station using a client/server mode, the wireless sensor being a client, and the central station being a server.

As a further improvement of the present invention, in the step B, the wireless sensor sends the collected physiological parameters to the designated receiving end; if the central station does not receive the physiological parameter sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

The present invention also provides a selective data transmission system based on a central monitoring system, including a wireless sensor, wherein the wireless sensor includes the following modules:

a collection module: configured to collect data;

a sending module: configured to send the data to a designated receiving end, the designated receiving end being a central station or a monitor;

a receiving end selection module: configured to select a receiving end according to an instruction of the central station, and take the receiving end as the designated receiving end;

a wireless connection module: configured to establish a wireless connection with the designated receiving end; and a return execution module: configured to return to execute the collection module;

judge whether a bedside monitoring instruction of the central station is received in the receiving end selection module; if yes, then execute a bedside monitoring mode unit; otherwise, execute a central monitoring mode unit;

the bedside monitoring mode unit including:

a wireless connection monitor: Configured to establish a wireless connection with the monitor, and take the monitor as the designated receiving end; and a return execution unit: configured to return to execute the collection module;

the central monitoring mode unit including:

judging whether a central monitoring instruction of the central station is received; if yes, then executing a wireless connection central station module; otherwise, returning to execute the collection module;

the wireless connection central station module: configured to establish a wireless connection with the central station, and take the central station as the designated receiving end; and a return execution module: configured to return to execute the collection module;

in the step sending module, if the designated receiving end is the monitor, then after the wireless sensor sends the data to the monitor, the monitor transmits the received data to the central station.

As a further improvement of the present invention, the bedside monitoring mode step further includes generating a warning signal to make the wireless sensor alarm.

In one embodiment, the device further includes:

a wireless sensor configuration module: configured to save following configuration information in the wireless sensor: a wireless sensor device number, an IP address and a port number of the central station, as well an IP address and a port number of the monitor; wherein the wireless sensor device number is configured to control data parameters of the wireless sensor to be displayed in a sub-window corresponding to the device number on the central station; the IP address and the port number of the central station are configured to establish a TCP connection between the wireless sensor and the central station; the IP address and the port number of the monitor are configured to establish a TCP connection between the wireless sensor and the monitor; and the configuration information is read after the wireless sensor is electrified and enabled; and a module of establishing a TCP connection between the wireless sensor and the central station: the wireless sensor sends a connection request to the IP address and the port number of the central station, and establishes a TCP connection, wherein the wireless sensor communicates with the central station using a client/server mode, the wireless sensor being a client, and the central station being a server.

As a further improvement of the present invention, the selective data transmission method further includes a central station, wherein the central station includes all wireless sensor device number and monitor device number, the central station intercepts a TCP port number, receives a connection request from the wireless sensor and the monitor, and establishes a TCP connection; and the central station establishes an independent TCP communication channel for each new connection request, so that the central station is capable of receiving the network data of multiple sets of wireless sensors and multiple sets of monitors simultaneously; and the wireless sensor and the monitor communicate with the central station using a client/server mode, the wireless sensor being a client, and the central station being a server.

As a further improvement of the present invention, in the sending module, the wireless sensor sends the collected physiological parameters to the designated receiving end; if the central station does not receive the physiological parameter sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

The present invention has the advantages that: The method and the system according to the present invention realize selective transmission of data through transmitting the data to a selected receiving end, and the working modes can be switched; therefore, the wireless sensor can work in various mode, working nodes can be switched; therefore, the wireless sensor can work under various modes, the data transmitted by the wireless sensor can select a receiver, and the working modes are diversified and can be switched, thus facilitating a user to use.

DETAILED DESCRIPTION OF THE PREFERRED EMBODIMENTS

Figure 1:
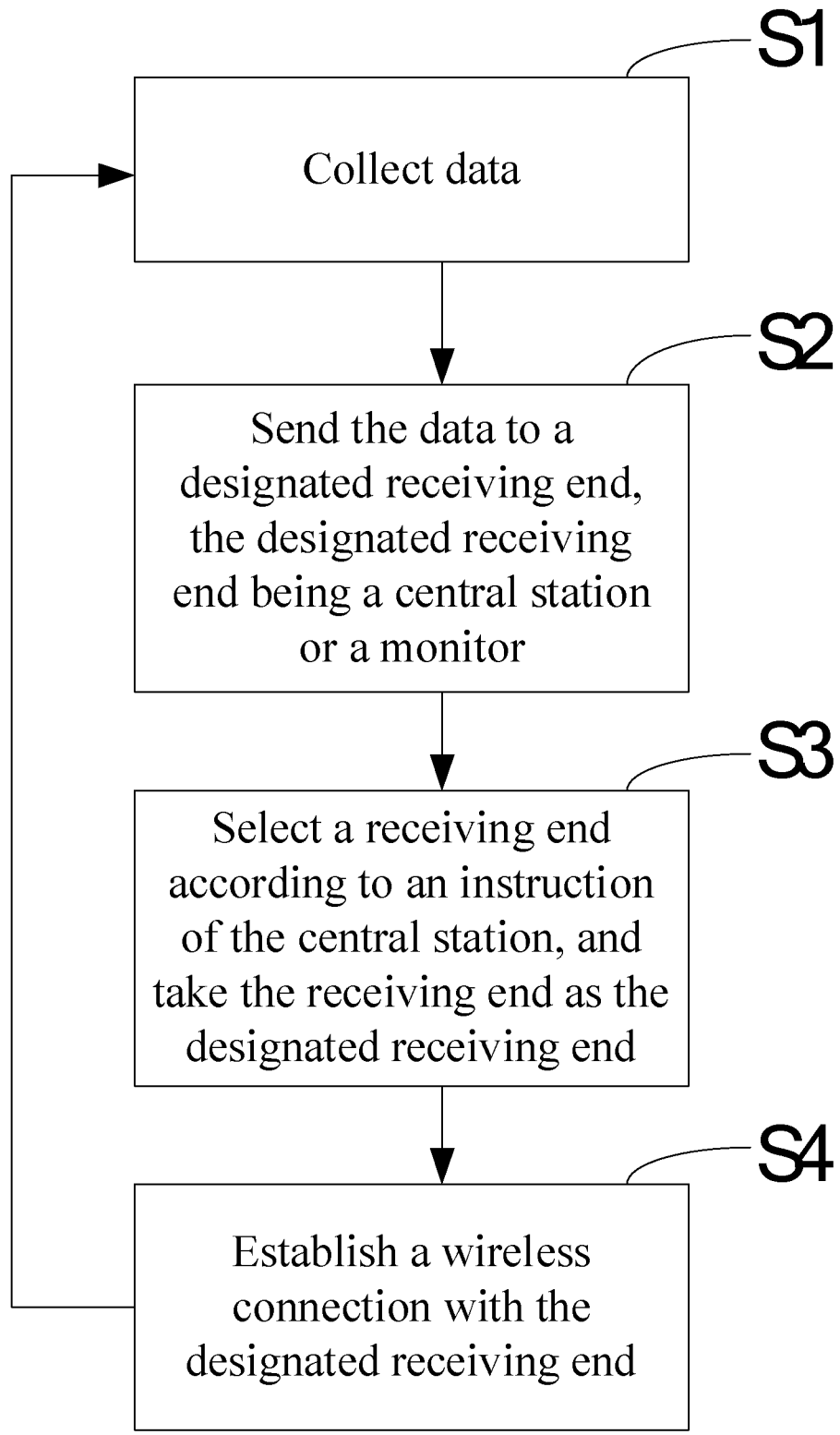
FIG. 1 is a flow chart of a method of the present invention.

As shown in FIG. 1, the present invention discloses a selective data transmission method based on a selective data transmission method, wherein the selective data transmission method includes a wireless sensor, and the wireless sensor executes the following steps of:
S1. collecting data; S2. sending the data to a designated receiving end, the designated receiving end being a central station or a monitor; S3. selecting a receiving end according to an instruction of the central station, and taking the receiving end as the designated receiving end; S4. establishing a wireless connection with the designated receiving end; and S4. then returning to execute step S1.

Figure 2:
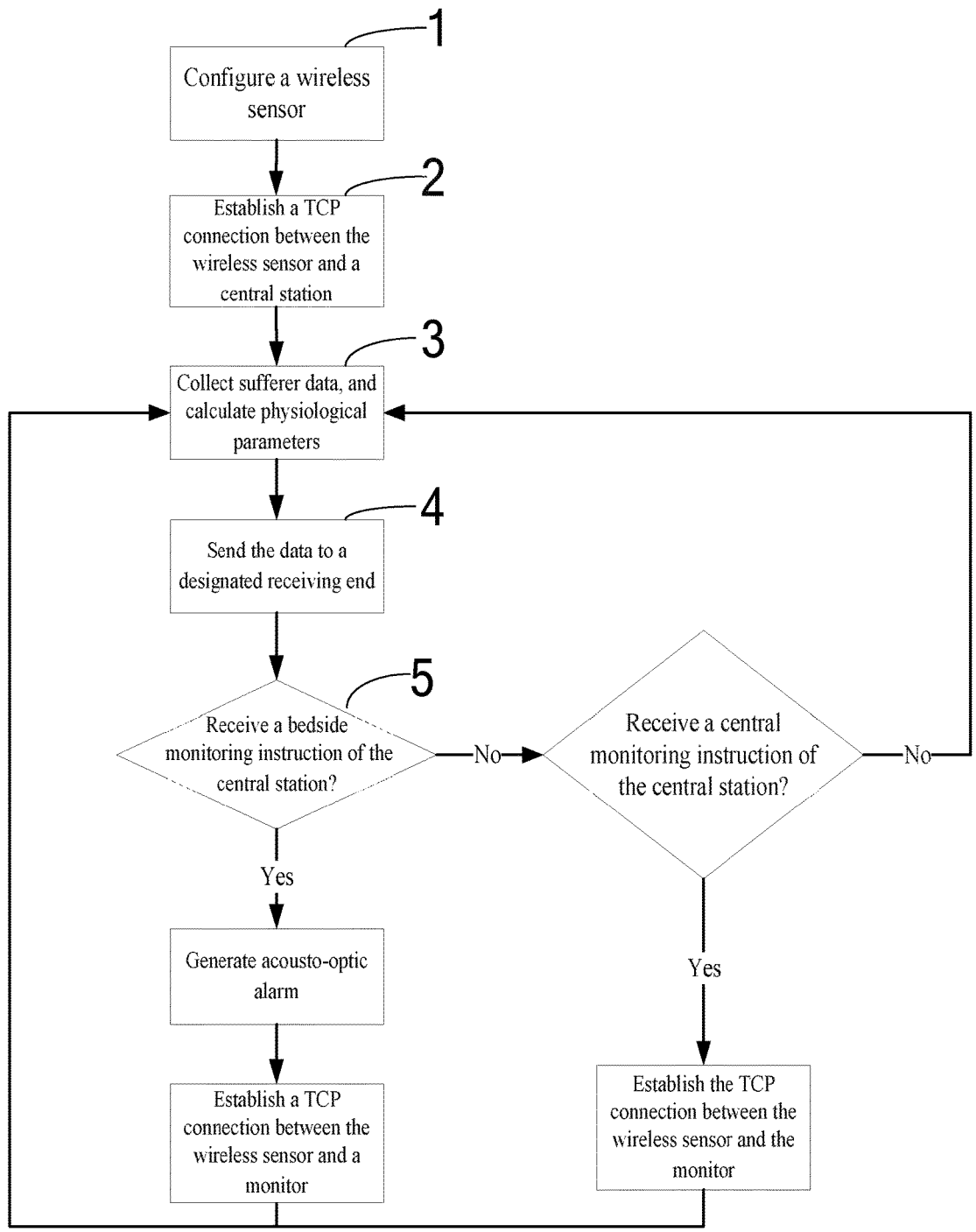
FIG. 2 is a working flow chart of a wireless sensor of the present invention.

As shown in FIG. 2, and as one embodiment of the present invention, before the step S1, the method further includes the following two steps of:
a first step-wireless sensor configuration step: the following configuration information is saved in the wireless sensor: a wireless sensor device number, an IP address and a port number of the central station, as well an IP address and a port number of the monitor; wherein the wireless sensor device number is configured to control data parameters of the wireless sensor to be displayed in a sub-window corresponding to the device number on the central station; the IP address and the port number of the central station are configured to establish a TCP connection between the wireless sensor and the central station; the IP address and the port number of the monitor are configured to establish a TCP connection between the wireless sensor and the monitor; and the configuration information is read after the wireless sensor is electrified and enabled; and the wireless sensor device number is a positive integer between 1 and 100;
a second step-step of establishing a TCP connection between the wireless sensor and the central station; the wireless sensor sends a connection request to the IP address and the port number of the central station, and establishes a TCP connection, wherein the wireless sensor communicates with the central station using a client/server mode, the wireless sensor being a client, and the central station being a server.
a third step is a specific embodiment of step S1, wherein in the third step, sufferer data is collected, and physiological parameters are calculated. The wireless sensor includes an ultrasound sensor, a pressure sensor, an electro-cadiography sensor, a non-invasive blood pressure sensor, a blood oxygen sensor, a body temperature sensor and sensors of other types.

A fourth step is a specific embodiment of step S2, wherein in the fourth step, the data is sent to a designated receiving end, and the wireless sensor packs the physiological parameters in each second, wherein the data packet includes the following fields: wireless sensor device number-physiological parameter type code-physiological parameter, wherein the wireless sensor device number is obtained in step 1, and the physiological parameter type code is configured to mark the type of the physiological parameter, for example, 100 represents a fetal heart rate, 200 represents a uterine pressure, the physiological parameter is obtained in the third step, then the data packet is sent to the designated receiving end through a TCP/IP protocol.

A fifth step is a specific embodiment of step S3, wherein in step S3, the central station is a controller; a bedside monitoring instruction of the central station is judged whether to be received in the fifth step; if yes, then a bedside monitoring mode step is executed; otherwise, a central monitoring mode step is executed; and
a specific method for judging whether a bedside monitoring instruction of the central station is received in the fifth step is as follows: checking whether a bedside monitoring instruction data packet exists in a UDP received data buffer zone of a wireless sensor network module, the bedside monitoring instruction data packet containing the following fields: wireless sensor device number-instruction type code, an instruction type code 1 representing a bedside monitoring instruction. If the bedside monitoring instruction data packet exists, the data packet is parsed according to a protocol, and the following fields are obtained: wireless sensor device number and instruction type code; if the wireless sensor device number of the data packet is equal to the device number of the sensor, and the instruction type code is equal the bedside monitoring instruction, then the bedside monitoring instruction is received; otherwise, the bedside monitoring instruction is not received.

The bedside monitoring mode step includes the following steps of:
generating a warning signal to make the wireless sensor alarm; for example, acousto-optic alarm is executed, wherein a buzzer sounds periodically and a pilot lamp flashes periodically to remind that a pregnant woman needs to return an intensive care unit for receiving reinforced monitoring at a bedside machine and the central station;
establishing a wireless connection with the monitor, and taking the monitor as the designated receiving end, wherein the wireless sensor sends a connection request to the IP address and the port number of the monitor, and establishes a TCP connection, wherein the wireless sensor communicates with the monitor using a client/server mode, the wireless sensor being a client, and the monitor being a server; and disconnects the TCP connection with the central station after the wireless sensor establishes the TCP connection with the monitor; and
returning to execute the third step.

The central monitoring mode step includes the following steps of: judging whether a central monitoring instruction of the central station is received; if yes, then executing the following step; otherwise, returning to execute the third step;
a specific method for the wireless sensor judges whether receiving the central monitoring instruction of the central station is as follows: checking whether a central monitoring instruction data packet exists in the UDP received data buffer zone of the wireless sensor network module, the central monitoring instruction data packet containing the following fields: wireless sensor device number-instruction type code, an instruction type code 2 representing a central monitoring instruction. If the central monitoring instruction data packet exists, the data packet is parsed according to a protocol, and the following fields are obtained: wireless sensor device number and instruction type code; if the wireless sensor device number of the data packet is equal to the device number of the sensor, and the instruction type code is equal to the central monitoring instruction, then the central monitoring instruction of the central station is received; otherwise, the central monitoring instruction of the central station is not received.

If the central monitoring instruction of the central station is received, then the following steps are executed:

establishing a wireless connection with the central station, and taking the central station as the designated receiving end, i.e., the wireless sensor sends a connection request to the IP address and the port number of the central station, and establishes a TCP connection; the wireless sensor communicates with the central station using a client/server mode, the wireless sensor being a client, and the central station being a server; the wireless sensor disconnects the TCP connection with the monitor after establishing the TCP connection with the central station; and returning to execute the third step;

in the step S2, if the designated receiving end is the monitor, then after the wireless sensor sends the data to the monitor, the monitor transmits the received data to the central station.

FIG. 2 is one embodiment of the present invention, wherein the embodiment is mainly applied to sufferer monitoring.

Figure 3:
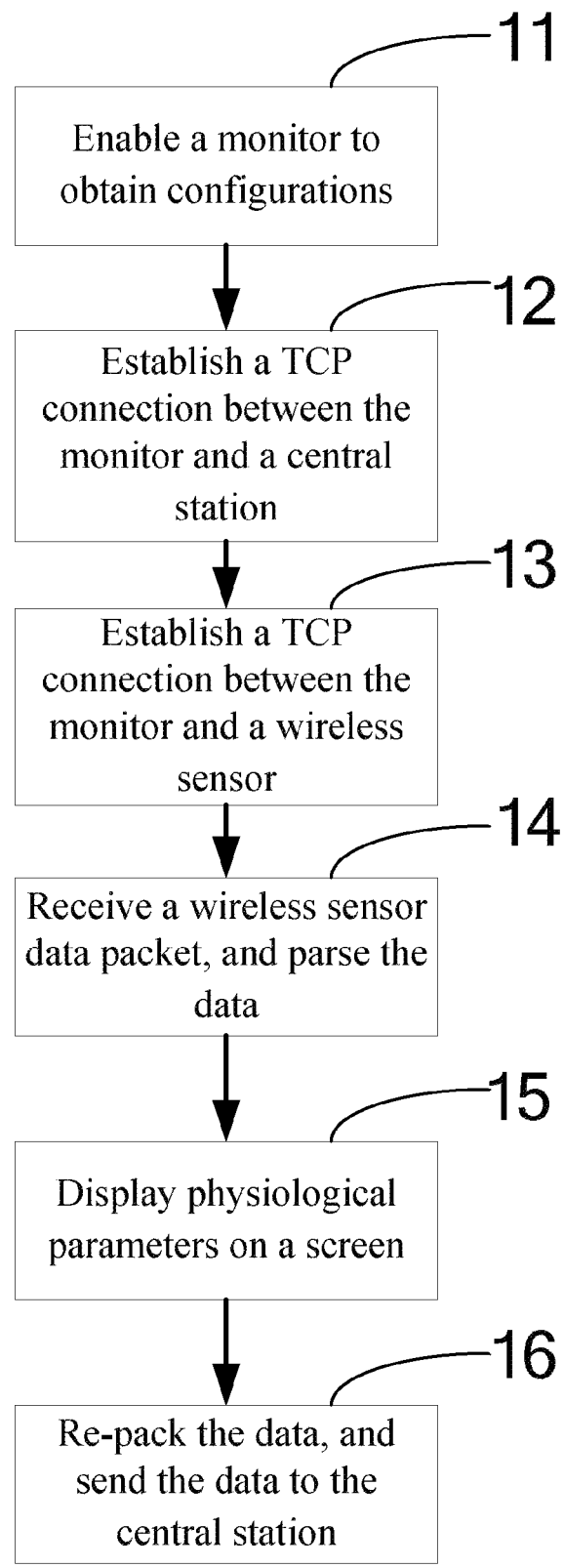
FIG. 3 is a working flow chart of a monitor of the present invention.

As shown in FIG. 3, the working flow of a monitor of the present invention is as follows:

step 11: enabling the monitor to obtain configurations, and then executing step 12.

In step 11, such information as a monitor device number, the IP address and the port number of a central station and the like are saved in a monitor configuration module. The monitor device number is a positive integer between 101 and 200, being configured to control data parameters of the monitor to be displayed in a sub-window corresponding to the device number on the central station; the IP address and the port number of the central station are configured to establish a TCP connection between the monitor and the central station. The configuration information is read from the monitor configuration module after the wireless sensor is electrified and enabled. Then step 12 is executed.

Step 12: the monitor establishes a TCP connection with the central station, and then step 13 is executed.

In step 12, the monitor sends a connection request to the IP address and an interception port number of the central station, and establishes a TCP connection; the monitor communicates with the central station using a client/server mode, the monitor being a client, and the central station being a server. Then step 13 is executed.

Step 13: the monitor establishes a TCP connection with a wireless sensor, and then step 14 is executed.

In step 13, the monitor intercepts the TCP port number, accepts a connection request from the wireless sensor, and establishes a TCP connection; the wireless sensor communicates with the monitor using a client/server mode, the wireless sensor being a client, and the monitor being a server. Then step 14 is executed.

Step 14: the monitor receives a wireless sensor data packet and parses data; then step 15 is executed.

In step 14, if the monitor receives the data packet sent by the wireless sensor, the monitor parses the data packet according to a protocol and obtains the following fields: wireless sensor device number-physiological parameter type code-physiological parameter, then step 15 is executed.

Step 15: the monitor displays the physiological parameters on a screen, and then step 16 is executed.

In step 15, the monitor displays a physiological parameter type on the screen according to the physiological parameter type code of the data packet, for example, the type code 100 displays as "fetal heart rate", then the physiological parameter is displayed below the "fetal heart rate". Then step 16 is executed.

Step 16: the monitor packs the data again and sends the data to the central station.

In step 16, the monitor packs the physiological parameters again in each second, wherein the data packet includes the following fields: monitor device number-physiological parameter type code-physiological parameter, wherein the monitor device number is obtained in step 11, the physiological parameter type code and the physiological parameter are obtained in step 14, and then the data packet is sent to the central station through a TCP/IP protocol.

Figure 4:
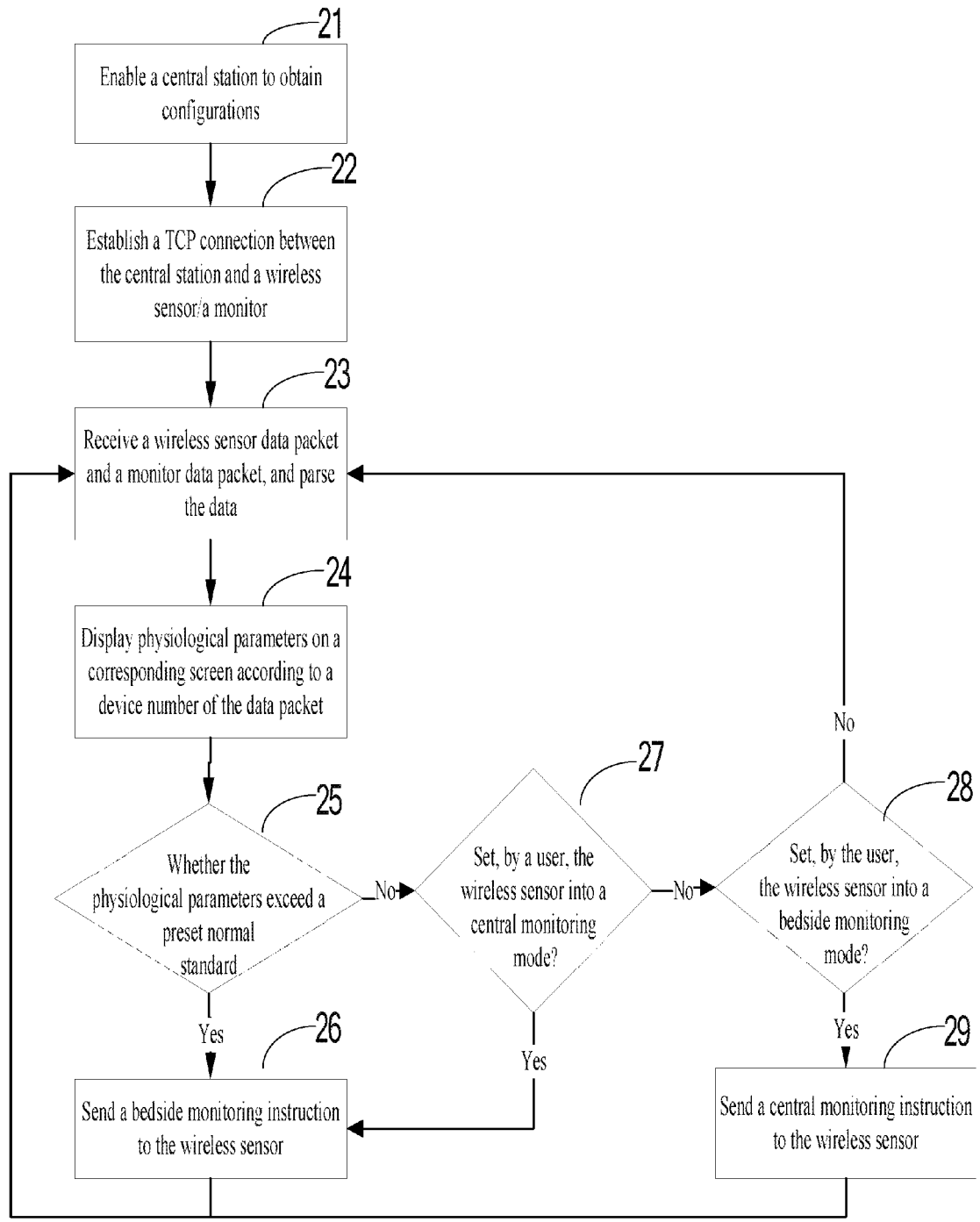
FIG. 4 is a working flow chart of a central station of the present invention.

As shown in FIG. 4, the working flow of the central station according to the present invention is as follows:

step 21: the central station is enabled to obtain configurations, and then step 22 is executed.

In step 21, all the device numbers are saved in a central station configuration module, including all the wireless sensor device numbers and monitor device numbers as well as the normal standards of various physiological parameters. The device number is a positive integer, being configured to control the data parameters of the wireless sensor or the monitor to be displayed in a sub-window corresponding to the device number on the central station; the wireless sensor device number ranges from 1 to 100, and the monitor device number ranges from 101 to 200. After the central station is electrified and enabled, the above information is read from the central station configuration module, and a screen window is initialized to distribute a sub-window for each device number which is configured to display the physiological parameter corresponding to the device number. Then step 22 is executed.

Step 22: the monitor establishes a TCP connection with the wireless sensor and/or monitor, and then step 23 is executed.

In step 22, the central station intercepts a TCP port number, receives a connection request from the wireless sensor and the monitor, and establishes a TCP connection; and the central station establishes an independent TCP communication channel for each new connection request, so that the central station is capable of receiving the network data of multiple sets of wireless sensors and multiple sets of monitors simultaneously; and the wireless sensor and the monitor communicate with the central station using a client/server mode, the wireless sensor being a client, and the central station being a server. Then step 23 is executed.

Step 23: the monitor receives a wireless sensor data packet and a monitor data packet, parses the data, and then step 24 is executed.

In step 23, if the central station receives the data packet sent by the wireless sensor or the monitor, the central station parses the data packet according to a protocol. For the wireless sensor data packet, the following fields can be obtained via parsing: wireless sensor device number-physiological parameter type code-physiological parameter. For the monitor data packet, the following fields can be obtained via parsing: monitor device number-physiological parameter type code-physiological parameter. Then step 24 is executed.

Step 24: the central station displays the physiological parameter in a corresponding window according to the device number of the data packet, and then step 5 is executed.

In step 24, the central station finds the sub-window on the screen corresponding to the device number according to the device number of the data packet, and then displays the physiological parameter type on the sub-window according to the physiological parameter type code of the data packet; for example, a type code 100 displays as "fetal heart rate", then the physiological parameter is displayed below the "fetal heart rate". Then step 25 is executed.

Step 25: the central station judges whether the physiological parameters from the wireless sensor exceed a preset normal standard.

In step 25, a user may preset the normal standards of various physiological parameters in advance in the central station, for example, a normal range of the fetal heart rate is 120-160, and an ultra limit duration is 30 s; if the fetal heart rate is less than 120 for more than 30 s continuously, or the fetal heart rate is greater than 160 for 30 s continuously, then the fetal heart rate is considered to exceed the preset normal standard. The normal standards of various physiological parameters are all obtained in step 21. The central station finds the data packet from the wireless sensor according to the device number of the data packet, wherein the characteristic of the data packet is that the device number is a positive integer between 1 and 100. The central station compares the physiological parameter obtained via parsing the data packet with the preset normal standard; if the physiological parameter exceeds the preset normal standard, then step 26 is executed; otherwise, step 27 is executed.

Step 26: the central station sends a bedside monitoring instruction to the wireless sensor, and then step 23 is executed.

In step 26, the central station generates a bedside monitoring instruction data packet, and sends the bedside monitoring instruction data packet to the wireless sensor through a UDP protocol via a broadcast mode. Then step 23 is executed. The bedside monitoring instruction data packet contains the following fields: wireless sensor device number-instruction type code, an instruction type code 1 represents a bedside monitoring instruction.

Step 27: The central station checks whether a user sets the wireless sensor in the bedside monitoring mode.

In step 27, the central station checks whether the monitoring mode of the wireless sensor is modified by the user. If checking that the user sets the monitoring mode option of the wireless sensor as the bedside monitoring mode, then step 26 is executed; otherwise, step 28 is executed.

Step 28: the central station checks whether the user sets the wireless sensor in the central monitoring mode.

In step 28, the central station checks whether the monitoring mode of the wireless sensor is modified by the user. If checking that the user sets the monitoring mode option of the wireless sensor as the central monitoring mode, then step 29 is executed; otherwise, step 23 is executed.

Step 29: the central station sends a central monitoring instruction to the wireless sensor, and then step 23 is executed.

In step 29, the central station generates a central monitoring instruction data packet, and sends the central monitoring instruction data packet to the wireless sensor through a UDP protocol via a broadcast mode. Then step 23 is executed. The central monitoring instruction data packet contains the following fields: wireless sensor device number-instruction type code, an instruction type code 2 represents a central monitoring instruction.

In the present invention and as another embodiment of the present invention, in step S1, the wireless sensor collects positioning data information; in step S2, the wireless sensor sends the positioning data information to the central station; in step S3, the wireless sensor selects a receiving end according to an instruction, and takes the receiving end as the designated receiving end; in step S4, a wireless connection with a designated receiving end is established. For example, there are three regions (A, B, C) in a hospital, wherein B is an infected area, then when a sufferer carries the wireless sensor to enter B, the wireless sensor collects the positioning data information, and transmits the positioning data information to the central station; the central station when determining that the sufferer is in the infected area, sends an instruction to the wireless sensor to command the wireless sensor to establish a wireless sensor with the monitor at this moment, and remind the sufferer to leave B and return beside the monitor to enter the bedside monitoring mode.

The present invention also provides a selective data transmission system based on a central monitoring system, including a wireless sensor, wherein the wireless sensor includes the following modules of:

a collection module: configured to collect data;

a sending module: configured to send the data to a designated receiving end;

a receiving end selection module: configured to select a receiving end according to an instruction of the central station, and take the receiving end as the designated receiving end;

a wireless connection module: configured to establish a wireless connection with the designated receiving end; and a return execution module: configured to return to execute the collection module.

In the receiving end selection module, an instruction of a controller is received, a receiving end is selected according to the instruction of the controller, and the receiving end is taken as a designated receiving end.

In the receiving end selection module, the controller is a central station; whether a bedside monitoring instruction of the central station is judged whether to be received in the receiving end selection module; if yes, then a bedside monitoring mode unit is executed; otherwise, a central monitoring mode unit is executed;

the bedside monitoring mode unit including:

an alarm unit: configured to generate a warning signal to make the wireless sensor alarm;

a wireless connection monitor: configured to establish a wireless connection with the monitor, and take the monitor as the designated receiving end; and a return execution unit: configured to return to execute the collection module;

the central monitoring mode unit including:

judging whether a central monitoring instruction of the central station is received; if yes, then executing a wireless connection central station module; otherwise, returning to execute the collection module;

the wireless connection central station module: configured to establish a wireless connection with the central station, and take the central station as the designated receiving end; and a return execution module: configured to return to execute the collection module;

in the step sending module, if the designated receiving end is the monitor, then after the wireless sensor sends the data to the monitor, the monitor transmits the received data to the central station.

the wireless sensor further includes:

a wireless sensor configuration module: configured to save following configuration information in the wireless sensor: a wireless sensor device number, an IP address and a port number of the central station, as well an IP address and a port number of the monitor; wherein the wireless sensor device number is configured to control data parameters of the wireless sensor to be displayed in a sub-window corresponding to the device number on the central station; the IP address and the port number of the central station are configured to establish a TCP connection between the wireless sensor and the central station; the IP address and the port number of the monitor are configured to establish a TCP connection between the wireless sensor and the monitor; and the configuration information is read after the wireless sensor is electrified and enabled; and a module of establishing a TCP connection between the wireless sensor and the central station: the wireless sensor sends a connection request to the IP address and the port number of the central station, and establishes a TCP connection, wherein the wireless sensor communicates with the central station using a client/server mode, the wireless sensor being a client, and the central station being a server.

the selective data transmission method further includes a central station, wherein the central station includes all wireless sensor device number and monitor device number, the central station intercepts a TCP port number, receives a connection request from the wireless sensor and the monitor, and establishes a TCP connection; and the central station establishes an independent TCP communication channel for each new connection request, so that the central station is capable of receiving the network data of multiple sets of wireless sensors and multiple sets of monitors simultaneously; and the wireless sensor and the monitor communicate with the central station using a client/server mode, the wireless sensor being a client, and the central station being a server.

FIG. 2 to FIG. 4 are implementation manners of the present invention in medical field. The implementation manners realize to access the wireless sensor and the monitor into the central station for central monitoring at the same time; the wireless sensor may also be accessed into the monitor for bedside monitoring; the applications of wireless sensor+central station and wireless sensor+monitor+central station are integrated into one; moreover, the application modes can be switched dynamically. The wireless sensor is responsible for collecting the physiological parameters of the sufferer, and then sending the physiological parameters to the monitor or the central station through a wireless network, so that the wireless sensor can be accessed to the monitor or the central station. The central station can receive the data packets from the monitor and the wireless sensor at the same time, and display the physiological parameters in the corresponding windows, so that the central station can be accessed to the monitor and the wireless sensor. Moreover, the central station can judge whether the physiological parameters from the wireless sensor exceed a preset normal standard (or, a doctor may also judge manually whether the normal value is exceeded through the physiological parameter from the wireless sensor exceeds the normal standard); if the normal value is exceeded, then a bedside monitoring instruction may be sent to the wireless sensor, to remind that a pregnant woman needs to return an intensive care unit for receiving reinforced monitoring at a bedside machine and the central station; after the health situation of the pregnant woman recovers well, the medical care personnel can send a central monitoring instruction to the wireless sensor through the central station, so as to switch to the application mode of wireless sensor+central station.

The method and the system according to the present invention has the advantageous effects that: 1. for the pregnant woman in a poor health condition, the medical care personnel may set the wireless sensor as to be accessed to the monitor to realize bedside tight monitoring of the sufferer; meanwhile, the monitor is accessed to the central station, so that the sickness of the pregnant woman can be monitored in real time at the central station, thus ensuring the security of the sufferer through dual monitoring. 2. For a pregnant woman in health condition, the medical care personnel can set the wireless sensor as to be accessed to the central station without a bedside machine for monitoring, and only the monitoring of the central station is needed, which reduces the workload of the medical care personnel, and improves the monitoring comfort of the pregnant woman. 3. In the central monitoring mode, if the health condition of the pregnant woman is abnormal, the central station can automatically remind that the pregnant woman needs to return the intensive care unit, and receive reinforced monitoring at the bedside machine and the central station, so that the security of the sufferer is ensured. 4. In the bedside monitoring mode, if the health condition of the pregnant woman recovers well, the medical care personnel can change the mode into the central station through the central station, which reduces the workload of the medical care personnel and improves the monitoring comfort of the pregnant woman.

The present invention has the advantageous effects that the method and the system realize selective data transmission through transmitting the data to a selected receiving end, which not only can be applied to the field of medical monitoring, but also can be applied to such fields as security prevention, data backup and the like; working nodes can be switched; therefore, the wireless sensor can work under various modes; the data transmitted by the wireless sensor can select a receiver, and the working modes are diversified and can be switched, thus facilitating a user to use.

The above-mentioned contents are further descriptions to the present invention with reference to the specific preferred embodiments, and it cannot be deemed that the specific implementation of the present invention are only limited to these descriptions. Those having ordinary skills in the art of the present invention may also make many simple deductions or replacements without departing from the conceive of the present invention which shall all fall within the protection scope of the present invention.

What is claimed is:

1. A selective data transmission method based on a selective data transmission method, comprising a wireless sensor, wherein the wireless sensor executes the following steps of:

A: collecting data; selecting, according to an instruction from a central station, and among the central station and a monitor, a receiving end of the collected data; and designating the selected receiving end as a designated receiving end;

B: sending the collected data to the designated receiving end;

D: establishing a wireless connection with the designated receiving end; and

E: returning to execute step A;

wherein step A further comprises judging if the instruction from the central station is for selecting a bedside monitoring mode or for selecting a central monitoring mode and, if the instruction is for selecting a bedside monitoring mode, then executing a bedside monitoring mode step; otherwise, executing a central monitoring mode step; the bedside monitoring mode step comprising the following steps of:

C1: establishing a wireless connection with the monitor, and designating the monitor as the designated receiving end; and C2: returning to execute step A;

the central monitoring mode step comprising the following steps of:

CC1) establishing a wireless connection with the central station, and designating the central station as the designated receiving end; and CC2) returning to execute step A;

wherein in the step B, if the designated receiving end is the monitor, then after the wireless sensor sends the collected data to the monitor, the monitor further transmits the collected data to the central station.

2. The selective data transmission method according to claim 1, wherein the bedside monitoring mode step further comprises generating a warning signal to make a wireless sensor alarm.

3. The selective data transmission method according to claim 2, wherein before the step A, the method further comprises the following two steps of:

a wireless sensor configuration step: following configuration information is saved in the wireless sensor: a wireless sensor device number, an Internet Protocol, IP, address and a port number of the central station, as well an IP address and a port number of the monitor, wherein the wireless sensor device number is configured to control data parameters of the wireless sensor to be displayed in a sub-window corresponding to the device number on the central station; the IP address and the port number of the central station are configured to establish a Transmission Control Protocol, TCP, connection between the wireless sensor and the central station; the IP address and the port number of the monitor are configured to establish a TCP connection between the wireless sensor and the monitor; and the configuration information is read after the wireless sensor is electrified and enabled; and a step of establishing a TCP connection between the wireless sensor and the central station: the wireless sensor sends a connection request to the IP address and the port number of the central station, and establishes a TCP connection, wherein the wireless sensor communicates with the central station using a client/server mode, the wireless sensor being a client, and the central station being a server.

4. The selective data transmission method according to claim 3, wherein the selective data transmission method comprises the central station, wherein the central station comprises all wireless sensor device number and monitor device number, the central station intercepts a TCP port number, receives a connection request from the wireless sensor and the monitor, and establishes a TCP connection; and the central station establishes an independent TCP communication channel for each new connection request, so that the central station is capable of receiving network data of multiple sets of wireless sensors and multiple sets of monitors simultaneously; and the wireless sensor and the monitor communicate with the central station using a client/server mode, the wireless sensor being a client, and the central station being a server.

5. The selective data transmission method according to claim 4, wherein in the step B, the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

6. The selective data transmission method according to claim 3, wherein in the step B, the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

7. The selective data transmission method according to claim 2, wherein in the step B, the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

8. The selective data transmission method according to claim 1, wherein in the step B, the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

9. A selective data transmission system based on a central monitoring system, comprising a wireless sensor, wherein the wireless sensor is configured to:
  collect data; select, according to an instruction from a central station, and among the central station and a monitor, a receiving end of the collected data; and designate the selected receiving end as a designated receiving end;
  send the collected data to the designated receiving end;
  establish a wireless connection with the designated receiving end; and
  return to collect data;
  wherein the wireless sensor is further configured to judge if the instruction from the central station is for selecting a bedside monitoring mode or for selecting a central monitoring mode, and, if the instruction is for selecting the bedside monitoring mode, then execute a bedside monitoring mode; otherwise, execute a central monitoring mode;
  wherein in the bedside monitoring mode:
  the wireless sensor further comprises a wireless connection module configured to establish a wireless connection with the monitor, and designate the monitor as the designated receiving end; and
  the wireless sensor comprises a return execution module configured to return to collect data;
  wherein in the central monitoring mode:
  the wireless connection module of the wireless sensor is configured to establish a wireless connection with the central station, and designate the central station as the designated receiving end; and
  the return execution module of the wireless sensor is configured to return to collect data; and
  wherein the selective data transmission system is further configured to, if the designated receiving end is the monitor, then after the wireless sensor sends the collected data to the monitor, execute the monitor to transmit the collected data to the central station.

10. The selective data transmission system according to claim 9, wherein the selective data transmission system is further configured to, in the bedside monitoring mode, generate a warning signal to make the wireless sensor alarm.

11. The selective data transmission system according to claim 10, wherein the wireless sensor further comprises:
  a wireless sensor configuration module configured to save following configuration information in the wireless sensor: a wireless sensor device number, an Internet Protocol, IP, address and a port number of the central station, as well an IP address and a port number of the monitor; wherein the wireless sensor device number is configured to control data parameters of the wireless sensor to be displayed in a sub-window corresponding to the device number on the central station; the IP address and the port number of the central station are configured to establish a Transmission Control Protocol, TCP, connection between the wireless sensor and the central station; the IP address and the port number of the monitor are configured to establish a TCP connection between the wireless sensor and the monitor; and the configuration information is read after the wireless sensor is electrified and enabled; and
  wherein the wireless sensor is further configured to establish a TCP connection between the wireless sensor and the central station: the wireless sensor configured to send a connection request to the IP address and the port number of the central station and establish a TCP connection, the wireless sensor configured to communicate with the central station using a client/server mode with the wireless sensor being a client and the central station being a server.

12. The selective data transmission system according to claim 11, wherein the selective data transmission system further comprises the central station, wherein the central station comprises all wireless sensor device number and monitor device number, the central station intercepts a TCP port number, receives a connection request from the wireless sensor and the monitor, and establishes a TCP connection; and the central station establishes an independent TCP communication channel for each new connection request, so that the central station is capable of receiving network data of multiple sets of wireless sensors and multiple sets of monitors simultaneously; and the wireless sensor and the monitor communicate with the central station using a client/server mode, the wireless sensor being a client, and the central station being a server.

13. The selective data transmission system according to claim 12, wherein the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

14. The selective data transmission system according to claim 11, wherein the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

15. The selective data transmission system according to claim 10, wherein the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

16. The selective data transmission system according to claim 9, wherein the wireless sensor sends the collected data to the designated receiving end, the collected data being physiological parameters; if the central station does not receive the physiological parameters sent by the wireless sensor within a predetermined time, the central station will alarm for prompting; if the central station receives the physiological parameters sent by the wireless sensor within the predetermined time, the central station compares the received physiological parameters with a preset normal standard; if the physiological parameters exceed the preset normal standard, the central station sends a bedside monitoring instruction; otherwise, the central station sends a central monitoring instruction.

* * * * *